(12) United States Patent
Casas

(10) Patent No.: US 10,744,246 B2
(45) Date of Patent: Aug. 18, 2020

(54) THERAPEUTIC UV BLOOD TREATMENT IN A BLOOD PUMP

(71) Applicant: HeartWare, Inc., Miami Lakes, FL (US)

(72) Inventor: Fernando Casas, Miami Lakes, FL (US)

(73) Assignee: HeartWare, Inc., Miami Lakes, FL (US)

(*) Notice: Subject to any disclaimer, the term of this patent is extended or adjusted under 35 U.S.C. 154(b) by 194 days.

(21) Appl. No.: 16/054,040

(22) Filed: Aug. 3, 2018

(65) Prior Publication Data

US 2019/0054221 A1 Feb. 21, 2019

Related U.S. Application Data

(60) Provisional application No. 62/547,358, filed on Aug. 18, 2017.

(51) Int. Cl.
*A61M 1/10* (2006.01)
*A61M 1/12* (2006.01)
*A61N 5/06* (2006.01)

(52) U.S. Cl.
CPC .......... *A61M 1/1036* (2014.02); *A61M 1/101* (2013.01); *A61M 1/1008* (2014.02); *A61M 1/1012* (2014.02); *A61M 1/122* (2014.02); *A61N 5/0601* (2013.01); *A61N 5/0624* (2013.01); *A61M 1/1015* (2014.02); *A61M 1/1017* (2014.02); *A61M 1/1086* (2013.01); *A61M 2205/053* (2013.01); *A61N 2005/0602* (2013.01)

(58) Field of Classification Search
CPC .... A61M 1/10; A61M 1/1012; A61M 1/1006; A61M 1/1008; A61M 1/1036; A61M 1/127; A61M 2205/053; A61M 1/12; A61M 1/122; A61M 1/1001; A61M 1/125; A61M 2025/09083; A61M 2025/09091; A61M 2025/09175; A61M 25/09; A61N 5/0624; A61N 5/0601; A61N 2005/0602
See application file for complete search history.

(56) References Cited

U.S. PATENT DOCUMENTS

| | | |
|---|---|---|
| 6,688,861 B2 | 2/2004 | Wampler |
| 7,575,423 B2 | 8/2009 | Wampler |
| 7,976,271 B2 | 7/2011 | LaRose et al. |

(Continued)

FOREIGN PATENT DOCUMENTS

WO 2016187145 A1 11/2016

OTHER PUBLICATIONS

International Search Report and Written Opinion dated Oct. 30, 2016, for corresponding International Application No. PCT/US2018/045107; International Filing Date; Aug. 3, 2018 consisting of 10 pages.

*Primary Examiner* — Amber R Stiles
(74) *Attorney, Agent, or Firm* — Christopher & Weisberg, P.A.

(57) ABSTRACT

An implantable blood pump including a housing having an inlet cannula, a rotor disposed within the housing, the rotor in fluid communication with the inlet cannula, a stator disposed within the housing, the stator configured to rotate the rotor when a current is applied to the stator, and at least one ultraviolet light emitter disposed within the housing.

17 Claims, 5 Drawing Sheets

(56) References Cited

U.S. PATENT DOCUMENTS

| | | |
|---|---|---|
| 8,007,254 B2 | 8/2011 | LaRose et al. |
| 8,419,609 B2 | 4/2013 | Shambaugh, Jr. et al. |
| 8,512,013 B2 | 8/2013 | LaRose et al. |
| 9,561,313 B2 | 2/2017 | Taskin |
| 2004/0186413 A1* | 9/2004 | Clark .................. A61L 2/0011 604/6.08 |
| 2011/0021966 A1* | 1/2011 | Leonard ............. A61M 1/3683 604/6.01 |
| 2013/0060188 A1 | 3/2013 | Bedwell et al. |
| 2015/0209498 A1* | 7/2015 | Franano ............. A61M 1/3659 600/16 |
| 2017/0281842 A1 | 10/2017 | LaRose et al. |

* cited by examiner

THERAPEUTIC UV BLOOD TREATMENT IN A BLOOD PUMP

CROSS-REFERENCE TO RELATED APPLICATION

This application is related to and claims priority to U.S. Provisional Patent Application Ser. No. 62/547,358, filed Aug. 18, 2017, entitled THERAPEUTIC UV BLOOD TREATMENT IN A BLOOD PUMP, the entirety of which is incorporated herein by reference.

FIELD

This disclosure relates to a method and system for providing therapeutic ultraviolet blood treatment in a blood pump.

BACKGROUND

Implantable blood pumps used as mechanical circulatory support devices or "MCSDs" include a pumping mechanism to move blood from the heart out to the rest of the body. The pumping mechanism may be a centrifugal flow pump, such as the HVAD® Pump manufactured by HeartWare, Inc. in Miami Lakes, Fla., USA. The HVAD® Pump is further discussed in U.S. Pat. No. 8,512,013, the disclosure of which is hereby incorporated in its entirety. In operation, the blood pump draws blood from a source such as the right ventricle, left ventricle, right atrium, or left atrium of a patient's heart and impels the blood into an artery such as the patient's ascending aorta or peripheral artery.

In an exemplary HVAD® Pump, an impeller is positioned within a housing having an upstream inflow cannula and a downstream outlet. The impeller is configured to rotate along an axis defined by the rotor and to impel blood upstream from the inflow cannula downstream to the outlet. In such a configuration, the impeller pumps blood in a direction substantially perpendicular to the axis about which it rotates. Dual stators are included in the pump, one upstream of the impeller and one downstream from the impeller and are each configured to rotate the impeller to impel blood. Disposed between the impeller and each respective stator is a non-ferromagnetic ceramic disk that separates the respective stator from the impeller and provides a smooth surface to pump blood. However, owing to the small gap between each ceramic disk and the impeller, the risk of thrombus increases as a result of potential stagnation of blood proximate the ceramic disk. Furthermore, the presence of bacteria in the blood also increases the risk of thrombus or infection, which may require medications, such as antibiotics, for treatment.

In another configuration, the pumping mechanism may be a flow pump which supports various flow types, such as the MVAD® Pump, also manufactured by HeartWare, Inc. in Miami Lakes, Fla., USA. The MVAD® Pump is further discussed in U.S. Pat. Nos. 8,007,254 and 9,561,313 and U.S. patent application Ser. No. 15/475,432, filed Mar. 31, 2017, the disclosure of which is hereby incorporated in its entirety. Blood flowing within the MVAD® Pump, like other MCSDs, is also subject to thrombus and infection.

SUMMARY

In one aspect, the present disclosure provides an implantable blood pump including a housing including an inlet cannula. A rotor is disposed within the housing, the rotor being in fluid communication with the inlet cannula. A stator is disposed within the housing, the stator being configured to rotate the rotor when a current is applied to the stator. At least one ultraviolet light emitter is disposed within the housing.

In another aspect, the disclosure provides a ceramic disk is disposed between the stator and the rotor, the ceramic disk includes the at least one ultraviolet light emitter being coupled thereto.

In another aspect, the disclosure provides the at least one ultraviolet light emitter is included on a flexible substrate.

In another aspect, the disclosure provides the flexible substrate is a sticker.

In another aspect, the disclosure provides the at least one ultraviolet light emitter is a printed material.

In another aspect, the disclosure provides the at least one ultraviolet light emitter is a stretchable material having a low profile.

In another aspect, the disclosure provides the inlet cannula includes an outer tube and an inner tube surrounded by the outer tube, the inner tube having an outer surface including the at least one ultraviolet light emitter coupled thereto.

In another aspect, the disclosure provides the inner tube is transparent.

In another aspect, the disclosure provides the ceramic disk includes a first surface facing away from the rotor and a second surface facing toward the rotor and the at least one ultraviolet light emitter is coupled to the first surface.

In another aspect, the disclosure provides the at least one ultraviolet light emitter is in communication with a source of power.

In one aspect, an implantable blood pump includes a housing including a first portion, a second portion upstream from the first portion, and an inflow cannula extending from the first portion to the second portion along an axis. A rotor is disposed within the housing for rotation about the axis. A first stator is disposed within the housing downstream from the rotor. A first ceramic disk is disposed within the housing between the first stator and the rotor. A second stator is disposed within the housing upstream from the rotor. A second ceramic is disk disposed between the second stator and the rotor. An ultraviolet light emitter is coupled to at least one of the group consisting of the first ceramic disk and the second ceramic disk, the ultraviolet light emitter being a flexible material.

In another aspect of the disclosure, the ultraviolet light emitter is included on a flexible substrate.

In another aspect of the disclosure, the flexible substrate is a sticker.

In another aspect of the disclosure, the ultraviolet light emitter is a printed material.

In another aspect of the disclosure, the ultraviolet light emitter is a stretchable material having a low profile.

In another aspect of the disclosure, the first ceramic disk includes a first surface facing away from the rotor and the ultraviolet light emitter is coupled to the first surface.

In another aspect of the disclosure, a second ultraviolet light emitter is included, and wherein the second ceramic disk includes a first surface facing away from the rotor and the second ultraviolet light emitter is coupled to the first surface.

In another aspect of the disclosure, the ultraviolet light emitter is in communication with a source of power.

In another aspect of the disclosure, at least one from the group consisting of the first ceramic disk and the second ceramic disk is translucent.

In one aspect, a method of providing therapeutic ultraviolet blood treatment in a blood pump includes emitting an ultraviolet light from an ultraviolet light emitter disposed within a housing of a blood pump.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
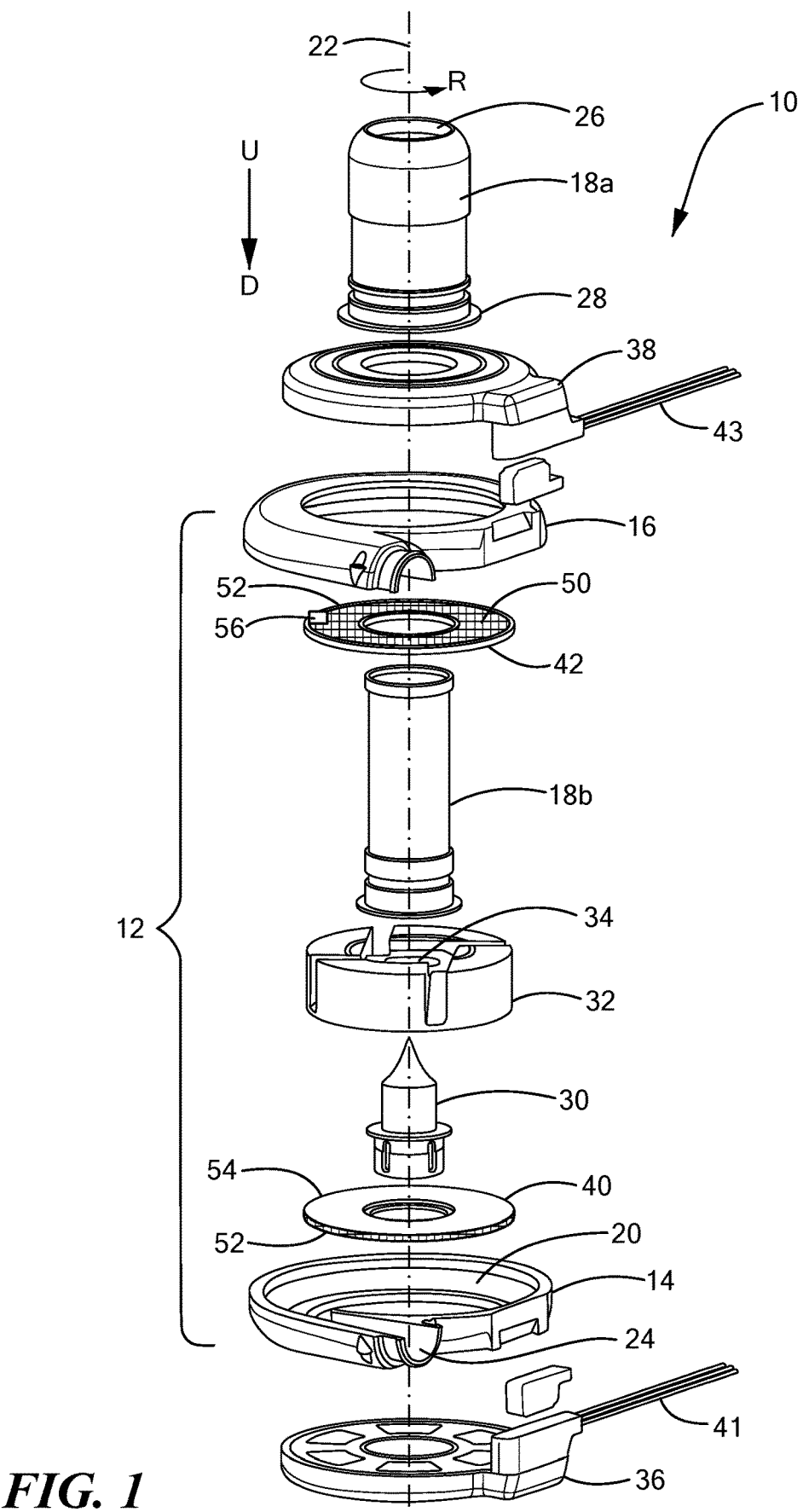
FIG. 1 is an exploded view of an exemplary blood pump constructed in accordance of the principles of the present application depicting at least one ultraviolet light emitter disposed within the blood pump.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before describing in detail exemplary embodiments, it is noted that the embodiments reside primarily in combinations of apparatus components and processing steps related to providing therapeutic ultraviolet blood treatment in an implantable blood pump. Accordingly, the system and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

Referring now to the drawings in which like reference designators refer to like elements there is shown in FIG. 1 an exemplary blood pump constructed in accordance with the principles of the present application and designated generally "10." The blood pump 10 according to one embodiment of the disclosure includes a static structure or housing 12 which houses the components of the blood pump 10. In one configuration, the housing 12 includes a lower housing or first portion 14, an upper housing or second portion 16, and an inlet portion or inflow cannula 18 which includes an outer tube 18a and an inner tube 18b. The first portion 14 and the second portion 16 cooperatively define a volute-shaped chamber 20 having a major longitudinal axis 22 extending through the first portion and inflow cannula 18. The chamber 20 defines a radius that increases progressively around the axis 22 to an outlet location on the periphery of the chamber 20. The first portion 14 and the second portion 16 define an outlet 24 in communication with chamber 20.

The first portion 14 and the second portion 16 also define isolated chambers (not shown) separated from the volute chamber 20 by magnetically permeable walls.

Figure 2:
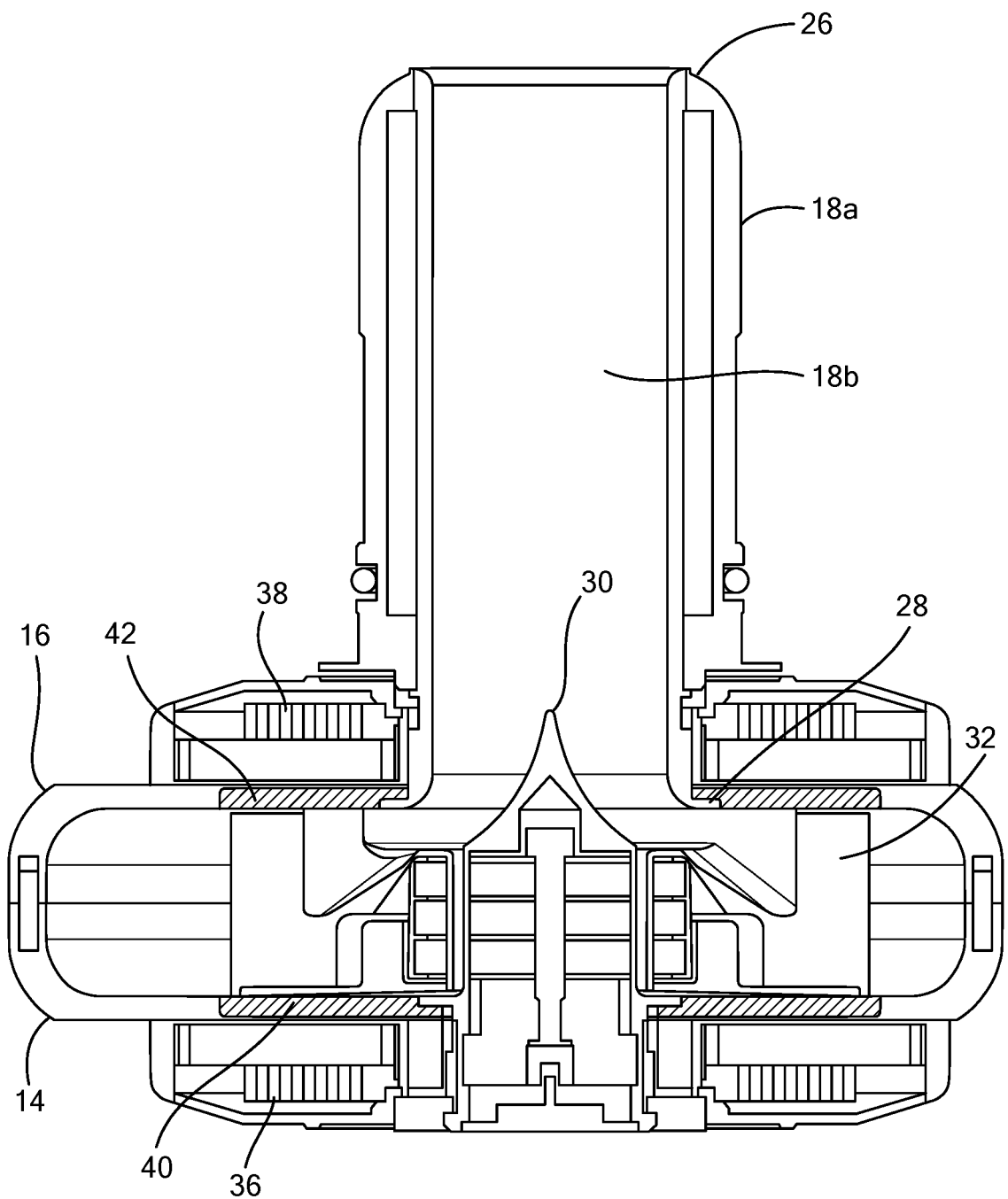
FIG. 2 is cross-sectional view of the assembled blood pump shown in FIG. 1.
Figure 3:
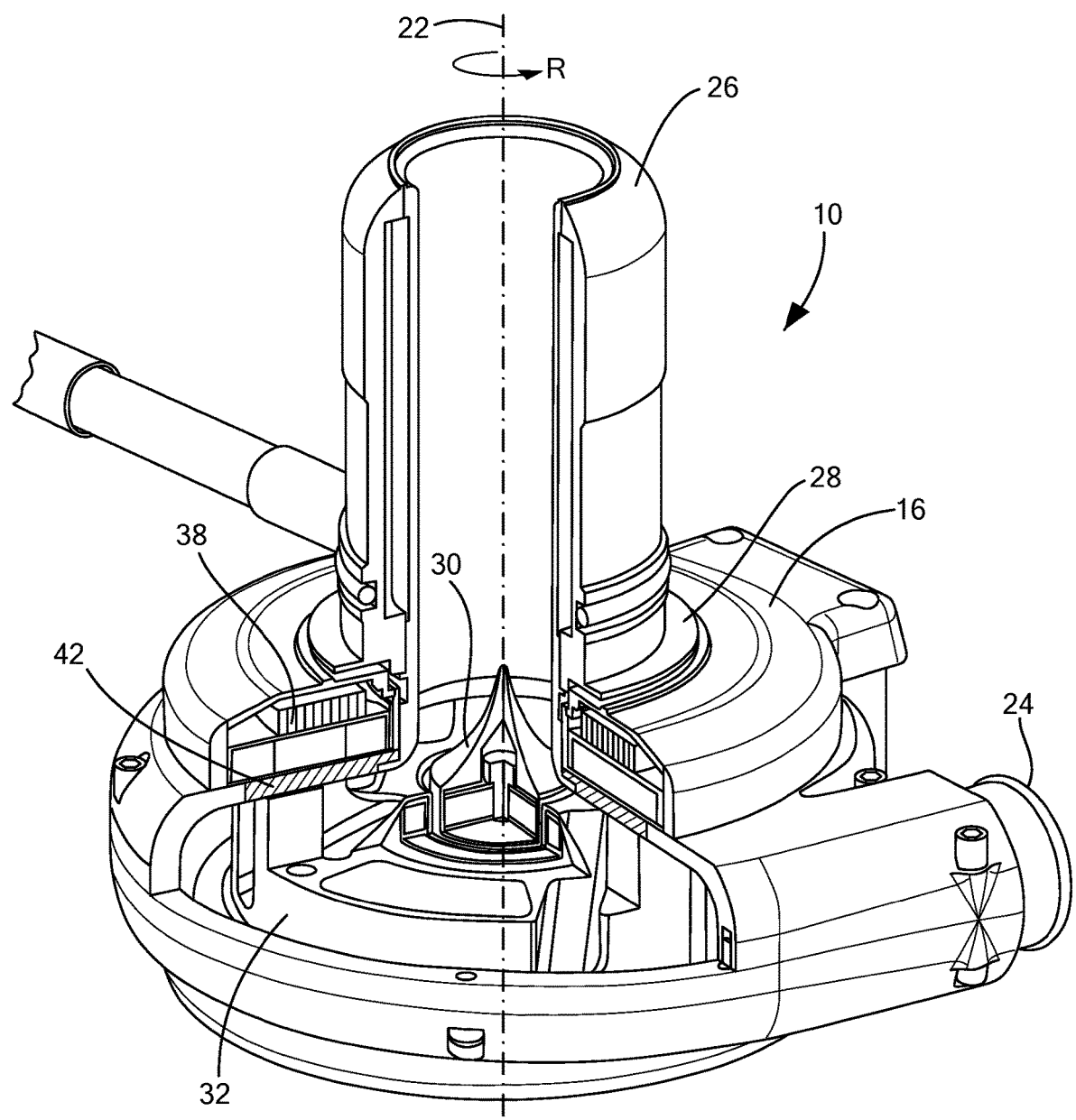
FIG. 3 is a slice cross-sectional view of the blood pump shown in FIG. 2.

Referring now to FIGS. 1-3, the inflow cannula 18 is generally cylindrical and extends from first portion 14 generally along the axis 22. The inflow cannula 18 has an upstream end or proximal end 26 remote from the second portion 16 and a downstream end or distal end 28 proximate the chamber 20. The parts of the housing 12 mentioned above are fixedly connected to one another so that the housing 12 as a whole defines a continuous enclosed flow path. The flow path extends from upstream end 26 at the upstream end of the flow path to the outlet 24 at the downstream end of the flow path. The upstream and downstream directions along the flow path are indicated in FIG. 1 by the arrows U and D respectively. A post 30 is mounted to first portion 14 along axis 22. A generally disc-shaped ferromagnetic rotor 32 with a central hole 34 is mounted within chamber 20 for rotation about the axis 22. The rotor 32 includes a permanent magnet and flow channels for transferring blood from adjacent the center of the rotor 32 to the periphery of the rotor 32. In the assembled condition, the post 30 is received in the central hole of the rotor 32. A first stator 36 having a at least two coils may be disposed within the first portion 14 upstream from the rotor 32. The first stator 36 may be axially aligned with the rotor along the axis 22 such that when a current is applied to the coils in the first stator 36, the electromagnetic forces generated by the first stator 36 rotate the rotor 32 and pump blood. A second stator 38 may be disposed within the second portion 16 downstream from the rotor 32. The second stator 38 may be configured to operate in conjunction with or independently of the first stator 36 to rotate the rotor 32.

Electrical connectors 41 and 43 (FIG. 1) are provided on first portion 14 and second portion 16 respectively, for connecting the coils to a source of power such as a controller (not shown). The controller is arranged to apply power to the coils of the pump to create a rotating magnetic field which spins rotor 32 around axis 22 in a predetermined first direction of rotation, such as the direction R indicated by the arrow in FIG. 1, i.e., counterclockwise as seen from the upstream end of inflow cannula 18. In other configurations of the blood pump 10, the first direction may be clockwise. Rotation of the rotor 32 impels blood downstream along the flow path so that the blood, moves in a downstream direction D along the flow path, and exits through the outlet 24. During rotation, hydrodynamic and magnetic bearings (not shown) support the rotor 32 and maintain the rotor 32 out of contact with the surfaces of the elements of the first portion 14 and the second portion 16 during operation. The general arrangement of the components described above may be similar to the blood pump 10 sold under the designation HVAD® by HeartWare, Inc., assignee of the present application. The arrangement of components such as the magnets, electromagnetic coils, and hydrodynamic bearings used in such a pump and variants of the same general design are described in U.S. Pat. Nos. 6,688,861; 7,575,423; 7,976,271; and 8,419,609, the disclosures of which are hereby incorporated by reference.

Referring to FIGS. 1 and 2, a first non-ferromagnetic disk 40 may be disposed within the first portion 14 downstream from the rotor 32 between the first stator 36 and the rotor 32. A second non-ferromagnetic disk 42 may be disposed upstream from the rotor 32 within the second portion 16 between the second stator 38 and the rotor 32. The first and second disks 40 and 42 may be composed of a ceramic material which is attached to the first portion 14 or the second portion 16 of the housing 12.

In order to therapeutically treat blood moving along the flow path with ultraviolet light, one or more ultraviolet light emitters 50 may be disposed within the housing 12 and coupled to the first disk 40 and/or the second disk 42. The ultraviolet light emitters 50 may be sensors, lamps, lasers, or another suitable light source configured to shine ultraviolet light onto the blood to administer therapeutic treatments. The therapeutic treatments may include, but are not limited to, anti-bacterial treatments and anti-thrombus treatments, which may decrease the need for medications, such as antibiotics. For example, as shown in FIG. 1, the ultraviolet light emitters 50 may be included on or otherwise define a flexible substrate or circuit, such as a sticker, that is adhered to or stretched around the first disk 40 and/or the second disk 42. The ultraviolet light emitters 50 and/or the flexible substrate may also be made of a stretchable material having a low profile that occupies minimal space, thus allowing the ultraviolet light emitters 50 to be coupled to non-traditional substrates, such as the first disk 40. In another configuration, the ultraviolet light emitters 50 may be a printed material that is reproduced onto the first disk 40 and/or the second disk 42 using etching, printing, or the like.

In one configuration, the first disk 40 and the second disk 40 include a first surface 52 facing away from the rotor 32 and a second surface 54 facing toward the rotor 32. The first surface 52 is sealed within the respective first portion 14 or the second portion 16 out of the blood flow path. In other words, blood is out of contact with the first surface 52. Accordingly, in blood pumps such as the HVAD®, the ultraviolet light emitters 50 may be coupled to the first surface 52 and may define an ultraviolet light path or field extending from the first surface 52 through the second surface 54 onto the blood within the housing 12. In one configuration, the direction of the ultraviolet light path emitted from the first disk 40 may be from the downstream direction to the upstream direction, whereas the direction of the ultraviolet light path emitted from the second disk 42 may be from the upstream direction to the downstream direction, as indicated by the arrows U and D respectively. The direction of the ultraviolet light path emitted from the first disk 40 and the second disk 42 may be adjusted and is not limited to a particular light path. The first disk 40 and the second disk 42 may be translucent and/or transparent to ultraviolet light, thus allowing the ultraviolet light path or field to shine through onto the blood.

The ultraviolet light emitters 50 may be in communication with a source of power, such as a battery or electricity. For example, the ultraviolet light emitters 50 may be wired to a battery disposed within the housing 12. The battery may be rechargeable by a transcutaneous energy transfer (TET) system or another charging method. In another configuration, the source of power 56 may be electricity provided through one or more of the coils of the electrical connector 41 connected to the controller (not shown). In the alternative, the source of power 56 may be a driveline separate from the electrical connector 41 which connects to the controller or another external power source. The ultraviolet light emitters 50 may be continuously in use or may be periodically activated by the controller.

Figure 4:
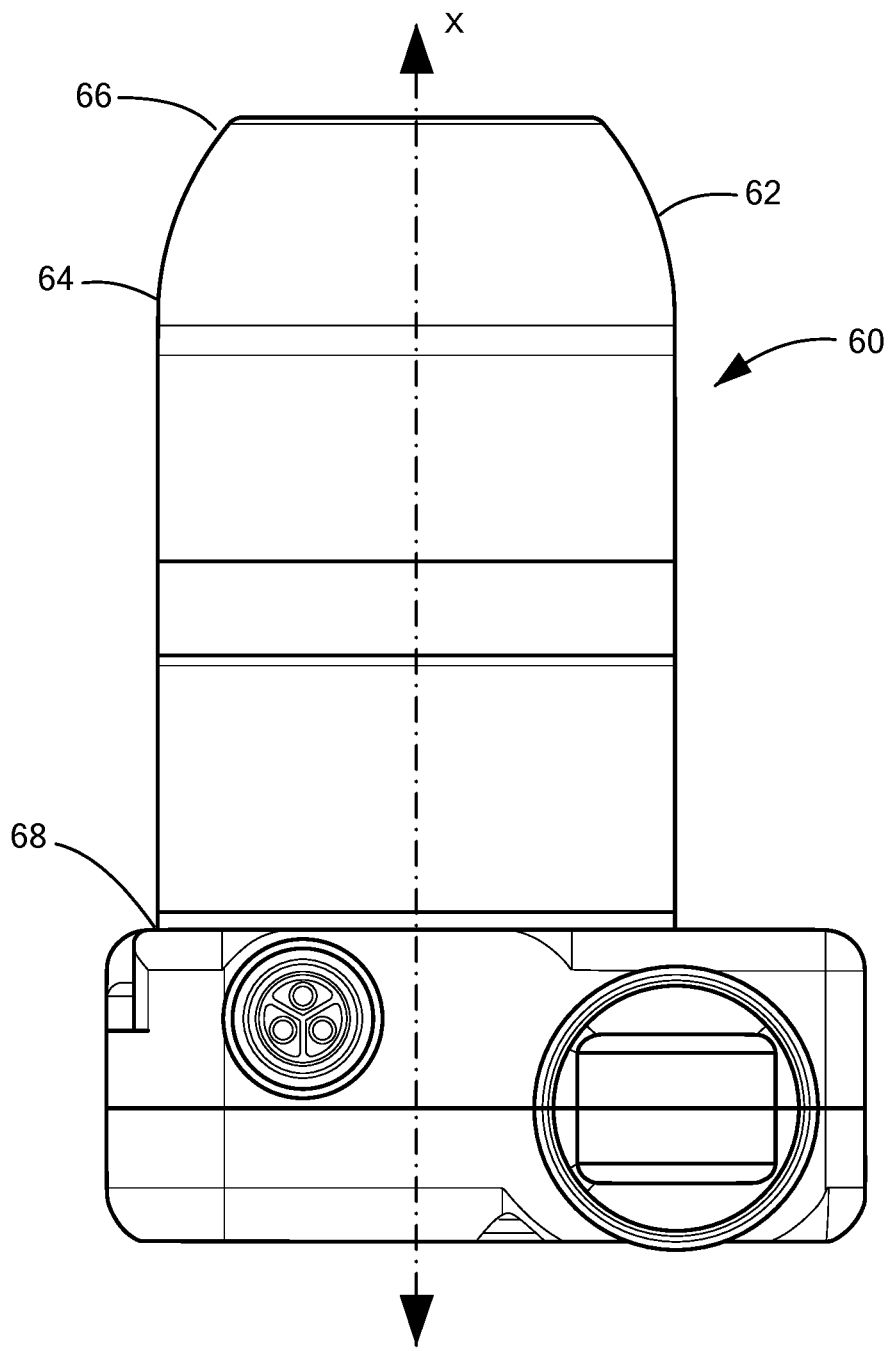
FIG. 4 is a side view of another exemplary blood pump configured to provide therapeutic ultraviolet blood treatment.

With reference to FIG. 4, another configuration of an exemplary blood pump configured to provide therapeutic ultraviolet blood treatment is provided and designed generally as "60." The blood pump 60 includes a housing 62 and an inlet or inflow cannula 64. The housing 62 may define a first major longitudinal axis or housing axis ("x") extending from a proximal end 66 configured to be positioned within the heart to a distal end 68.

Figure 5:
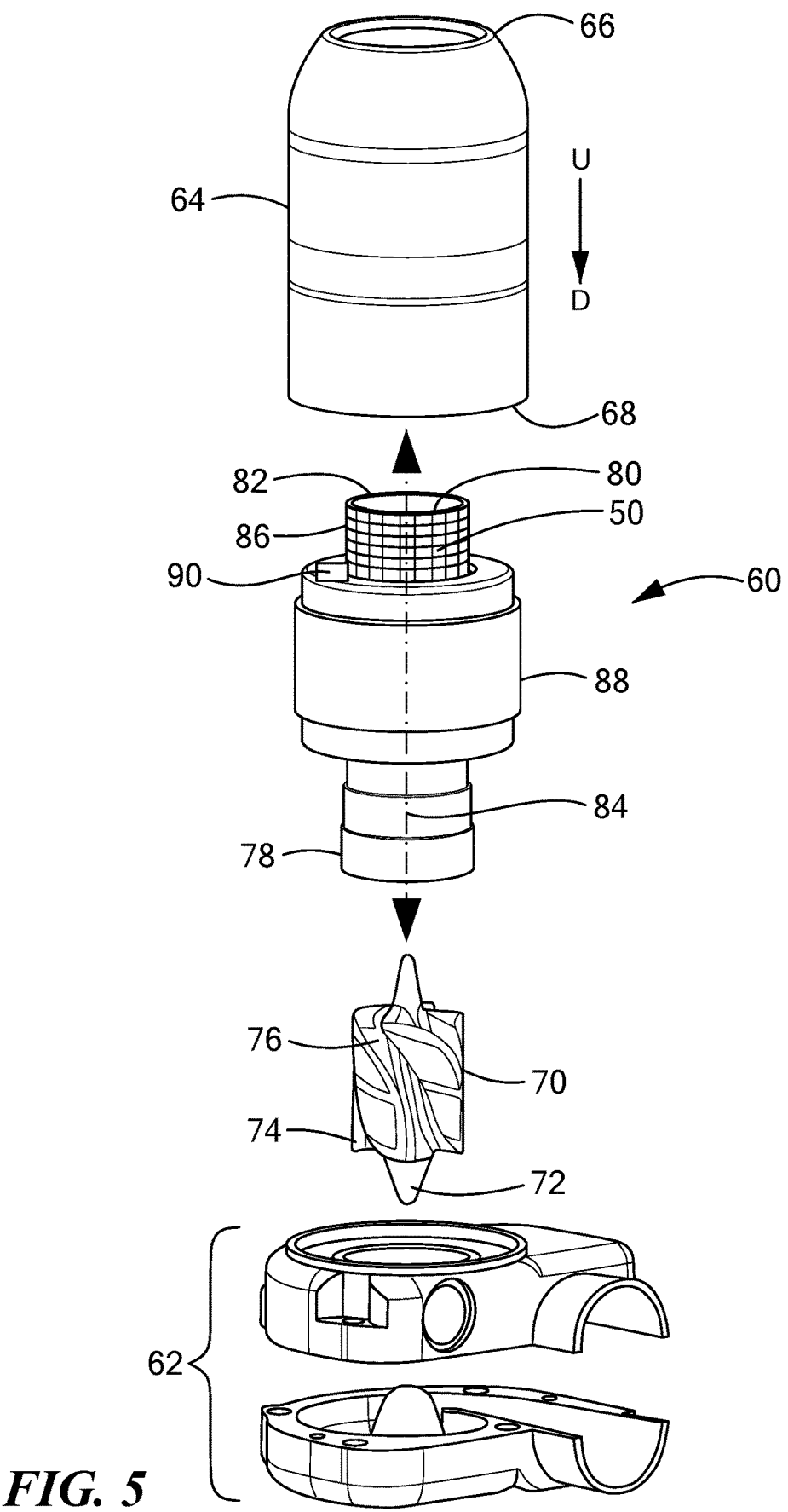
FIG. 5 is an exploded view of the blood pump shown in FIG. 4.

Referring to FIG. 5, disposed within the housing 62 is a ferromagnetic rotor 70 proximate to the distal end 68 of the inflow cannula 64 and configured to pump blood in a direction along the housing axis toward an outlet. The rotor 70 may include an axial flow impeller having a hub 72 including at least two blades 74 arranged circumferentially around the hub 72. The blades 74 define at least two channels 76 through which blood flows axially.

In one configuration, the inflow cannula 64 includes an inner tube 78 formed from a non-magnetic material, such as a ceramic, disposed within the housing 62. The inner tube 78 may include an interior surface 80 defining a cylindrical bore 82. The bore 82 has a bore axis 84 that is co-axial with the housing axis. The inner tube 78 also has a cylindrical outer surface 86 concentric with the bore axis 84. The bore 82 has an internal diameter just slightly larger than the maximum diameter of the rotor 70 such that the rotor 70 may be disposed within the bore 82. The pump 60 also includes a stator 88 having a cylindrical element encircling the inner tube 78 and the rotor 70. The stator 88 includes pole pieces which receive electrical current from a drive circuit (not shown) to spin the rotor 70, thus causing the blades 74 to drive the blood from an upstream direction U in a downstream direction D relative to the rotor 70 and the housing 62. The foregoing features and general mode of operation of the pump may be the same as those disclosed in U.S. Pat. Nos. 8,007,254 and 9,561,313, incorporated by reference herein, and used in axial flow blood pumps of the type sold under the designation MVAD® by Heartware, Inc., assignee of the present application.

In one configuration, the ultraviolet light emitters 50 may be coupled to the outer surface 86 of the inner tube 78. In the alternative, the ultraviolet light emitters 50 may be embedded within the inner tube 78. The methods of connecting the ultraviolet light emitters 50 to the inner tube 78 may be the same as those described above with respect to the first disk 40 and the second disk 42. Because the blood flow path within the housing 62 is through the bore 82 of the inner tube 78, the electrical components of the ultraviolet light emitters 50 are out of contact with the blood when disposed within the housing 62. The ultraviolet light path or field may travel from the outer surface 86 onto the blood within the inner tube 78. The inner tube 78 may be translucent and/or transparent to ultraviolet light, thus allowing the ultraviolet light path or field to shine through onto the blood.

In one configuration, as shown in FIG. 5, the ultraviolet light emitters 50 may be in communication with a source of power 90, such as a battery or electricity. For example, the ultraviolet light emitters 50 may be wired to a battery disposed within the housing 62. Similar to that described above with respect to the blood pump 10, the battery may be rechargeable by a transcutaneous energy transfer (TET) system or another charging method. In another configuration, the source of power 90 may be electricity provided through an electrical connector (not shown). In the alternative, the source of power 90 may be a driveline (not shown) separate from the electrical connector. The ultraviolet light emitters 50 may be continuously in use or may be periodically activated by a controller (not shown).

It will be appreciated by persons skilled in the art that the present embodiments are not limited to what has been particularly shown and described herein above. In addition, unless mention was made above to the contrary, it should be noted that all of the accompanying drawings are not to scale. A variety of modifications and variations are possible in light of the above teachings.

What is claims is:

1. An implantable blood pump, comprising:
   a housing including an inlet cannula;
   a rotor disposed within the housing, the rotor being in fluid communication with the inlet cannula;
   a stator disposed within the housing, the stator being configured to rotate the rotor when a current is applied to the stator;
   one from the group consisting of a ceramic disk and a tube disposed between the stator and the rotor; and
   at least one ultraviolet light emitter disposed within the housing and coupled to the one from the group consisting of the ceramic disk and the tube.

2. The implantable blood pump of claim 1, wherein the at least one ultraviolet light emitter is included on a flexible substrate.

3. The implantable blood pump of claim 2, wherein the flexible substrate is a sticker.

4. The implantable blood pump of claim 2, wherein the at least one ultraviolet light emitter is a stretchable material having a low profile.

5. The implantable blood pump of claim 1, wherein the at least one ultraviolet light emitter is a printed material.

6. The implantable blood pump of claim 1, wherein the tube is translucent.

7. The implantable blood pump of claim 1, wherein the ceramic disk includes a first surface facing away from the rotor and a second surface facing toward the rotor and the at least one ultraviolet light emitter is coupled to the first surface.

8. The implantable blood pump of claim 1, wherein the at least one ultraviolet light emitter is in communication with a source of power.

9. An implantable blood pump, comprising:
   a housing including a first portion, a second portion upstream from the first portion, and an inflow cannula extending from the first portion to the second portion along an axis;
   a rotor disposed within the housing for rotation about the axis;
   a first stator disposed within the housing downstream from the rotor;
   a first ceramic disk disposed within the housing between the first stator and the rotor;
   a second stator disposed within the housing upstream from the rotor;
   a second ceramic disk disposed between the second stator and the rotor; and
   an ultraviolet light emitter coupled to at least one of the group consisting of the first ceramic disk and the second ceramic disk, the ultraviolet light emitter being a flexible material.

10. The implantable blood pump of claim 9, wherein the ultraviolet light emitter is included on a flexible substrate.

11. The implantable blood pump of claim 10, wherein the flexible substrate is a sticker.

12. The implantable blood pump of claim 11, wherein the ultraviolet light emitter is a stretchable material having a low profile.

13. The implantable blood pump of claim 9, wherein the ultraviolet light emitter is a printed material.

14. The implantable blood pump of claim 9, wherein the first ceramic disk includes a first surface facing away from the rotor and the ultraviolet light emitter is coupled to the first surface.

15. The implantable blood pump of claim 14, further including a second ultraviolet light emitter, and wherein the second ceramic disk includes a first surface facing away from the rotor and the second ultraviolet light emitter is coupled to the first surface.

16. The implantable blood pump of claim 15, wherein at least one from the group consisting of the first ceramic disk and the second ceramic disk is translucent.

17. The implantable blood pump of claim 9, wherein the ultraviolet light emitter is in communication with a source of power.

* * * * *